United States Patent
Menn

(10) Patent No.: US 10,792,040 B2
(45) Date of Patent: *Oct. 6, 2020

(54) ARTICULATING STEERABLE CLIP APPLIER FOR LAPAROSCOPIC PROCEDURES

(71) Applicant: CONMED CORPORATION, Utica, NY (US)

(72) Inventor: Pavel Menn, Marblehead, MA (US)

(73) Assignee: CONMED CORPORATION, Utica, NY (US)

( * ) Notice: Subject to any disclaimer, the term of this patent is extended or adjusted under 35 U.S.C. 154(b) by 214 days.

This patent is subject to a terminal disclaimer.

(21) Appl. No.: 15/852,037

(22) Filed: Dec. 22, 2017

(65) Prior Publication Data

US 2018/0116664 A1    May 3, 2018

Related U.S. Application Data

(60) Division of application No. 14/339,021, filed on Jul. 23, 2014, now Pat. No. 9,918,715, which is a
(Continued)

(51) Int. Cl.
*A61B 17/10* (2006.01)
*A61B 17/128* (2006.01)
*A61B 17/00* (2006.01)

(52) U.S. Cl.
CPC .......... *A61B 17/10* (2013.01); *A61B 17/1285* (2013.01); *A61B 2017/00314* (2013.01); *A61B 2017/00323* (2013.01)

(58) Field of Classification Search
CPC ... A61B 17/10; A61B 17/128; A61B 17/1285; A61B 17/28; A61B 17/2804; A61B 17/29; A61B 2017/0488; A61B 2017/049; A61B 2017/2901; A61B 2017/2947; A61B 2017/00292; A61B 2017/003; A61B 2017/00305; A61B 2017/00309; A61B 2017/00314; A61B 2017/00318; A61B 2017/00323; A61B 2017/00327
See application file for complete search history.

(56) References Cited

U.S. PATENT DOCUMENTS

| 5,749,828 A * | 5/1998 | Solomon .............. A61B 1/0055 600/139 |
| 9,918,715 B2 * | 3/2018 | Menn ................. A61B 17/1285 |
| 2008/0132761 A1 * | 6/2008 | Sonnenschein ...... A61B 1/0055 600/142 |

* cited by examiner

*Primary Examiner* — Melanie R Tyson
(74) *Attorney, Agent, or Firm* — Bond, Schoeneck & King, PLLC; Frederick J. M. Price

(57) ABSTRACT

A long articulating steerable clip applier affixed to a user-operated handle. A surgical jaw assembly is attached to the other end of the clip applier. The clip applier is composed of articulating phalanges that are connected end to end by pivoting links and capable of angulations relative to one another when subjected to a tensile force. Each phalange has opposing s-shaped exterior grooves that form two continuous spiral-shaped channels for holding tension wires once the phalanges are assembled. Multiple tension wires are attached to opposite ends of adjacent phalanges. When each wire is pulled, this tensile force causes the phalanges to pivot at equivalent angles with each other. As each individual phalange pivots by an equivalent angle, the sum of these angles causes the free end of the clip applier to pivot by a large angle or a cascading actuation effect.

12 Claims, 19 Drawing Sheets

Related U.S. Application Data continuation of application No. 13/080,998, filed on Apr. 6, 2011, now abandoned.

(60) Provisional application No. 61/321,233, filed on Apr. 6, 2010.

ARTICULATING STEERABLE CLIP APPLIER FOR LAPAROSCOPIC PROCEDURES

CROSS REFERENCE TO RELATED APPLICATION

This application is a divisional of U.S. application Ser. No. 14/339,021 filed Jul. 23, 2014 and claims priority to U.S. Continuation application Ser. No. 13/080,998, filed Apr. 6, 2011, and U.S. Provisional Patent Application No.: 61/321,233 filed on Apr. 6, 2010, the contents of which are incorporated herein by reference.

FIELD OF THE INVENTION

This invention relates to a novel articulating steerable clip applier for laparoscopic or endoscopic procedures.

BACKGROUND OF INVENTION

Laparoscopic and endoscopic procedures are conducted through a small incision in the skin or natural body orifices.

In order to operate on a given tissue or a blood vessel, surgeons must ligate or occlude blood vessels to prevent patient blood loss. Surgical clip appliers are used in these surgeries for the application of hemostatic clips to ligate vessels. Clip appliers hold a surgical clip in an open position in a pair of specially adapted jaws. Once these jaws, containing clips, are positioned over a vessel, the clip is manually released over the vessel to ligate it. Inaccuracies in movement or failure to securely occlude the clip to the vessel can result damage to vessels or tissues, internal bleeding, lethal drops in blood pressure, infections, or longer recovery periods.

These instruments need to provide precise and accurate movement in order to ligate vessels within the body that are difficult to access. Instruments are needed that are narrow enough to be inserted through a small opening (such as an incision, trocar or natural body orifice), long enough to reach the desired internal tissues, and flexible enough to provide a wide range of motion to navigate the distal end of a clip applier with jaws containing loaded clips around body tissues to advance towards the internal operation site.

Accordingly, the subject invention discloses an improved steerable articulating surgical clip applier. It contains a long, narrow, distal articulating disposable portion that is inserted into a patient during surgery. This distal articulating portion is removably attached to a proximal non-disposable control unit for moving the long disposable portion within the patient and operating actuators to control the articulation and ligation of the clip applier.

By separating these two components, the risk of cross contamination between separate patients or separate tissues on the same patient is reduced. The non-disposable control unit does not enter the patient and the contaminated long and narrow component is simply disposed after each surgical procedure is completed. In addition, costs are saved since medical providers only need to replace the disposable component between surgical procedures.

SUMMARY OF THE INVENTION

There are additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

The subject invention discloses an endoscopic surgical tool having a handle and a shaft member coupled to the handle and extending along a shaft axis from a proximal end to a distal end, wherein the distal end of the shaft member is adapted to receive an end effector, comprising: A. a linear array of n phalanx sections, where n is an integer greater than 2, wherein the linear array includes a sequentially aligned proximal phalanx section, n−2 intermediate phalanx sections, and a distal phalanx section, wherein the ith phalanx section, wherein i is greater than or equal to 1 and less than or equal to n, extends along an associated central axis $CA_i$ between a proximal end $PE_i$ and a distal end DEL and includes: a tubular member $TM_i$ defining a. a central void region $CVR_i$ extending along the central axis $CA_i$ between the proximal end $PE_i$ and the distal end DEL and b. an exterior surface $ES_i$ disposed about the central void region $CVR_i$ and extending along the central axis $CA_i$ from the proximal end $PE_i$ to the distal end DEL wherein the n phalanx sections are aligned whereby the central axis $CA_i$ of each phalanx section intersects with the central axis of phalanx sections adjacent thereto in the linear array, B. an end effector coupler EEC disposed at the distal end of the distal phalanx section and adapted for coupling the distal end to an end effector, C. a base coupling assembly BC disposed at the proximal end of the proximal phalanx section and adapted to couple to the proximal end of the proximal phalanx section to the distal end of the shaft member, whereby the shaft axis intersects the central axis of the proximal phalanx section and whereby the proximal phalanx section is movable with respect to the distal end of the shaft member substantially only in rotational motion about a transverse axis TAO perpendicular to the central axis of the proximal phalanx section, D. n−1 phalanx section coupling assemblies PC, wherein each phalanx section coupling assembly is associated with an intermediate phalanx section and wherein the coupling assembly $PC_i$ associated with the ith phalanx section couples a distal end of the ith phalanx section to the proximal end of the adjacent i+1th phalanx section whereby the proximal end of the i+1th phalanx section is movable with respect to the distal end of the ith phalanx section substantially only in rotational motion about a transverse axis $TA_i$ perpendicular to the central axis of the ith phalanx section, wherein $TA_i$ and TAO are mutually parallel, and wherein each of the base coupling assembly and the n−1 phalanx coupling assemblies are operative whereby a torque applied to the proximal end of the proximal phalanx section about an axis parallel to transverse axis TAO, effects a same-direction angular rotational displacement of each of the ith phalanx sections with respect to the adjacent phalanx sections about the respective transverse axes $TA_i$.

In a further embodiment of the subject invention, the base coupling assembly BC may be adapted to detachably couple the proximal end of the proximal phalanx section to the distal end of the shaft member.

In another embodiment of the subject invention, the end effector coupling assembly EEC may be adapted to detachably couple the end effector to the distal end of the distal phalanx section.

In an additional embodiments of the subject invention, the ith phalanx section coupling assembly Ci may include: i. a coupling cam surface CCSi disposed about a cam central axis CCAi affixed to the distal end of the ith phalanx section, wherein the cam central axis CCAi is substantially coaxial with the transverse axis TAi, a substantially non-stretchable link coupling a point on the coupling cam surface of the ith phalanx section CCSPi with a point EPi+2 on the proximal end of the i+2th phalanx section, wherein point CCSPi and point EPi are disposed in a plane including CAi+1 and perpendicular to the transverse axes TAi and TAi+2 and on opposite sides central axis of the i+1 phalanx section CAi+1.

In a further embodiment of the subject invention, the link of coupling assembly Ci may be a cable extending between point CCSPi and point EPi+2.

In another embodiment of the subject invention, the cable extends in a helical path about the central axis CAi+1 between point CCSPi and point EPi+2.

In an additional embodiment of the subject invention, the exterior surface ESi includes an open-faced helical channel HCi+1 disposed about the central axis CAi+1, and the cable of coupling assembly Ci extends through the helical channel HCi+1.

In a further embodiment of the subject invention, the same-direction angular rotational displacement of each of the ith phalanx sections with respect to the adjacent phalanx sections are equi-angle.

In another embodiment of the subject invention, the tubular members TMi may be characterized by the same distance between the proximal end PEi and the distal end Dei.

In a further embodiment of the subject invention, at least two of the tubular members TMi may be characterized by different distances between their respective proximal ends PEi and distal ends Dei.

In an additional embodiment of the subject invention, the cam surfaces CCSi may be circular segments.

The subject invention also discloses an endoscopic surgical apparatus comprising: a handle having a front end and defining a longitudinal axis; an actuation member associated with the handle; an elongated articulating section comprising a plurality of interconnected pivotable vertebrae extending distally from the front end of said handle, wherein the plurality of pivotable vertebrae comprises an exterior surface, further wherein the plurality of pivotable vertebrae comprises an interior surface that defines a channel extending distally from the front end of said handle to a distal end to permit passage of surgical clips; and a tensioning system selectively operable from the actuation member to apply tensioning force to the plurality of interconnected pivotable vertebrae such that the proximal end of each interconnected pivotable vertebrae pivots at a substantially equivalent angle.

Another embodiment of the subject invention is an endoscopic surgical apparatus comprising: a handle having a front end and defining a longitudinal axis; an actuation member associated with the handle; an elongated articulating section comprising a plurality of interconnected pivotable vertebrae extending distally from the front end of said handle, wherein the plurality of pivotable vertebrae comprises an exterior surface, wherein each pivotable vertebrae comprises a set of opposing spiral-shaped grooves on the exterior surface such that the elongated articulating section has contiguous set of opposing spiral-shaped grooves, further wherein the plurality of pivotable vertebrae comprises an interior surface that defines a channel extending distally from the front end of said handle to a distal end to permit passage of surgical clips; and a plurality of tension wires inserted into the contiguous spiral-shaped grooves, wherein the plurality of tension wire are selectively operable from the actuation member to apply tensioning force to the plurality of interconnected pivotable vertebrae such that the proximal end of each interconnected pivotable vertebrae pivots at a substantially equivalent angle.

An additional embodiment of the subject invention is an endoscopic surgical apparatus comprising: a handle having a front end and defining a longitudinal axis; an actuation member associated with the handle; an elongated articulating section comprising a plurality of interconnected pivotable vertebrae extending distally from the front end of said handle, wherein the plurality of pivotable vertebrae comprises an exterior surface, wherein each pivotable vertebrae comprises a set of opposing spiral-shaped grooves on the exterior surface such that the elongated articulating section has contiguous set of opposing spiral-shaped grooves, further wherein the plurality of pivotable vertebrae comprises an interior surface that defines a channel extending distally from the front end of said handle to a distal end to permit passage of surgical clips; and a plurality of tension wires inserted into the contiguous spiral-shaped grooves, wherein the plurality of tension wire are selectively operable from the actuation member to apply tensioning force to the plurality of interconnected pivotable vertebrae such that the proximal end of each interconnected pivotable vertebrae pivots at a substantially equivalent angle.

A further embodiment of the subject invention discloses an endoscopic surgical apparatus comprising: a handle having a front end and defining a longitudinal axis; an actuation member associated with the handle; an elongated articulating section comprising a plurality of interconnected pivotable vertebrae extending distally from the front end of said handle, wherein the plurality of pivotable vertebrae comprises an exterior surface, further wherein the plurality of pivotable vertebrae comprises an interior surface that defines a channel extending distally from the front end of said handle to a distal end to permit passage of surgical clips; and a plurality of semi-circular ligaments placed over the plurality of pivotable vertebrae, wherein the plurality of semi-circular ligaments are selectively operable from the actuation member to apply tensioning force to the plurality of interconnected pivotable vertebrae such that the proximal end of each interconnected pivotable vertebrae pivots at a substantially equivalent angle.

Another embodiment of the subject invention is an endoscopic surgical apparatus comprising: a handle having a front end and defining a longitudinal axis; an actuation member coupled with the handle; an elongated articulating shaft coupled to the handle with a base coupling assembly and extending distally from the front end of said handle from a proximal end to a distal end, wherein the distal end of the articulating shaft is adapted to receive an end effector, the articulating shaft comprising a linear array of phalanx sections, wherein the linear array includes a sequentially aligned proximal phalanx section coupled on a distal end to the base coupling assembly, intermediate phalanx sections, and a distal phalanx section adapted to receive the end effector on the distal end, wherein each phalanx section comprises i) a proximal end and a distal end; ii) a central cavity extending along a central axis between the proximal end and the distal end; iii) an exterior surface; and iv) a set of opposing substantially spiral-shaped grooves on the exterior surface that extend along each phalanx from the proximal end to the distal end, wherein each the distal end of each phalanx section couples the proximal end of the adjacent phalanx section, whereby the proximal end of the phalanx section is movable with respect to the distal end of the phalanx section in rotational motion, and a plurality of tension wires inserted into the spiral-shaped grooves, wherein the plurality of tension wire are operable from the actuation member to apply tensioning force to the linear array of phalanx sections such that the proximal end of each phalanx section pivots at a substantially equivalent angle.

Another embodiment of the subject invention is an endoscopic surgical apparatus comprising: a handle having a front end and defining a longitudinal axis; an actuation member coupled with the handle; an elongated articulating shaft coupled to the handle with a base coupling assembly and extending distally from the front end of said handle from a proximal end to a distal end, wherein the distal end of the articulating shaft is adapted to receive an end effector, the articulating shaft comprising a linear array of phalanx sections, wherein the linear array includes a sequentially aligned proximal phalanx section coupled on a distal end to the base coupling assembly, intermediate phalanx sections, and a distal phalanx section adapted to receive the end effector on the distal end, wherein each phalanx section comprises i) a proximal end and a distal end; ii) a central cavity extending along a central axis between the proximal end and the distal end; iii) an exterior surface; wherein each the distal end of each phalanx section couples the proximal end of the adjacent phalanx section, whereby the proximal end of the phalanx section is movable with respect to the distal end of the phalanx section in rotational motion, and a plurality of semi-cylindrical ligaments placed over the plurality of phalanx sections, wherein the plurality of semi-cylindrical ligaments are selectively operable from the actuation member to apply tensioning force to the plurality of phalanx sections such that the proximal end of each phalanx section pivots at a substantially equivalent angle.

In embodiments of the subject invention, each phalanx or pivotable vertebrae may comprise a substantially cylindrical configuration.

In other embodiments of the subject invention, each phalanx or pivotable vertebrae may comprise a single piece.

In further embodiments of the subject invention, each phalanx or pivotable vertebrae may comprise two substantially half-cylindrical pieces.

In additional embodiments of the subject invention, the elongated articulating section may further comprise a distally attached surgical jaws assembly. In another embodiment the subject invention, the end effector may comprise a distally attached surgical jaws assembly.

In other embodiments of the subject invention, each pivotable vertebrae may project a first pivot member from the proximal end and project a second pivot member from the distal end, wherein the first pivot member of each pivotable vertebrae pivotably couples about a rotational axis to the second pivot member of a proximally adjacent pivotable vertebrae.

In further embodiments of the subject invention, the first pivot member may comprise a substantially cylindrical protrusion and the second pivot member may comprise a substantially cylindrical bore adapted for receiving the substantially cylindrical protrusion.

In other embodiments of the subject invention, each pivotable vertebrae may project a plurality of first pivot members from the proximal end and project a plurality of second pivot members from the distal end, wherein the plurality of first pivot members of each pivotable vertebrae pivotably couples about a rotational axis to the plurality of second pivot members of proximally adjacent pivotable vertebrae.

In additional embodiments of the subject invention, each phalanx section or pivotable vertebrae may be composed of injected-molded plastic.

In embodiments of the subject invention, the plurality of pivotable vertebrae fits within 3 mm to 10 mm envelope of MIS instrumentation.

In other embodiments of the subject invention, the plurality of tension wire may comprise a material selected from the group consisting of nickel titanium alloy, braided stainless steel, a single stainless steel wire, Kevlar, a high tensile strength monofilament thread, or combinations thereof.

In further embodiments of the subject invention, each tension wire attaches on a proximal end to a pivotable vertebrae proximate to the handle, extends through the spiral shaped grooves on a first subsequent adjacent distal pivotable vertebrae, and attaches on a distal end to a second subsequent adjacent distal pivotable vertebrae.

In additional embodiments of the subject invention, each tension wire proximally attaches on one side of the elongated articulating section to a pivotable vertebrae proximate to the handle, extends through the spiral shaped grooves on a subsequent adjacent distal pivotable vertebrae, and distally attaches on the opposing side of elongated articulating section to an opposing side of second subsequent adjacent distal pivotable vertebrae.

In other embodiments of the subject invention, applying force in the proximal direction to the proximal end of each tension wire rotates the second subsequent adjacent distal pivotable vertebrae, further wherein the direction of rotation is away from the side on the elongated articulating section that attaches to the proximal end of the tension wire.

In embodiments of the subject invention, applying force in the proximal direction to the proximal end of each tension wire rotates the second subsequent adjacent distal pivotable vertebrae, further wherein the direction of rotation is toward the side on the elongated articulating section that attaches to the distal end of the tension wire.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto. These together with other objects of the invention, along with the various features of novelty, which characterize the invention, are pointed out with particularity in the claims annexed to and forming a part of this disclosure.

BRIEF DESCRIPTION OF THE DRAWINGS

Advantages of the present invention will be apparent from the following detailed description of embodiments thereof, which description should be considered in conjunction with the accompanying drawings, in which.

DETAILED DESCRIPTION OF THE EMBODIMENTS

While several variations of the present invention have been illustrated by way of example in particular embodiments, it is apparent that further embodiments could be developed within the spirit and scope of the present invention, or the inventive concept thereof. However, it is to be expressly understood that such modifications and adaptations are within the spirit and scope of the present invention, and are inclusive, but not limited to the following appended claims as set forth.

Figure 1:
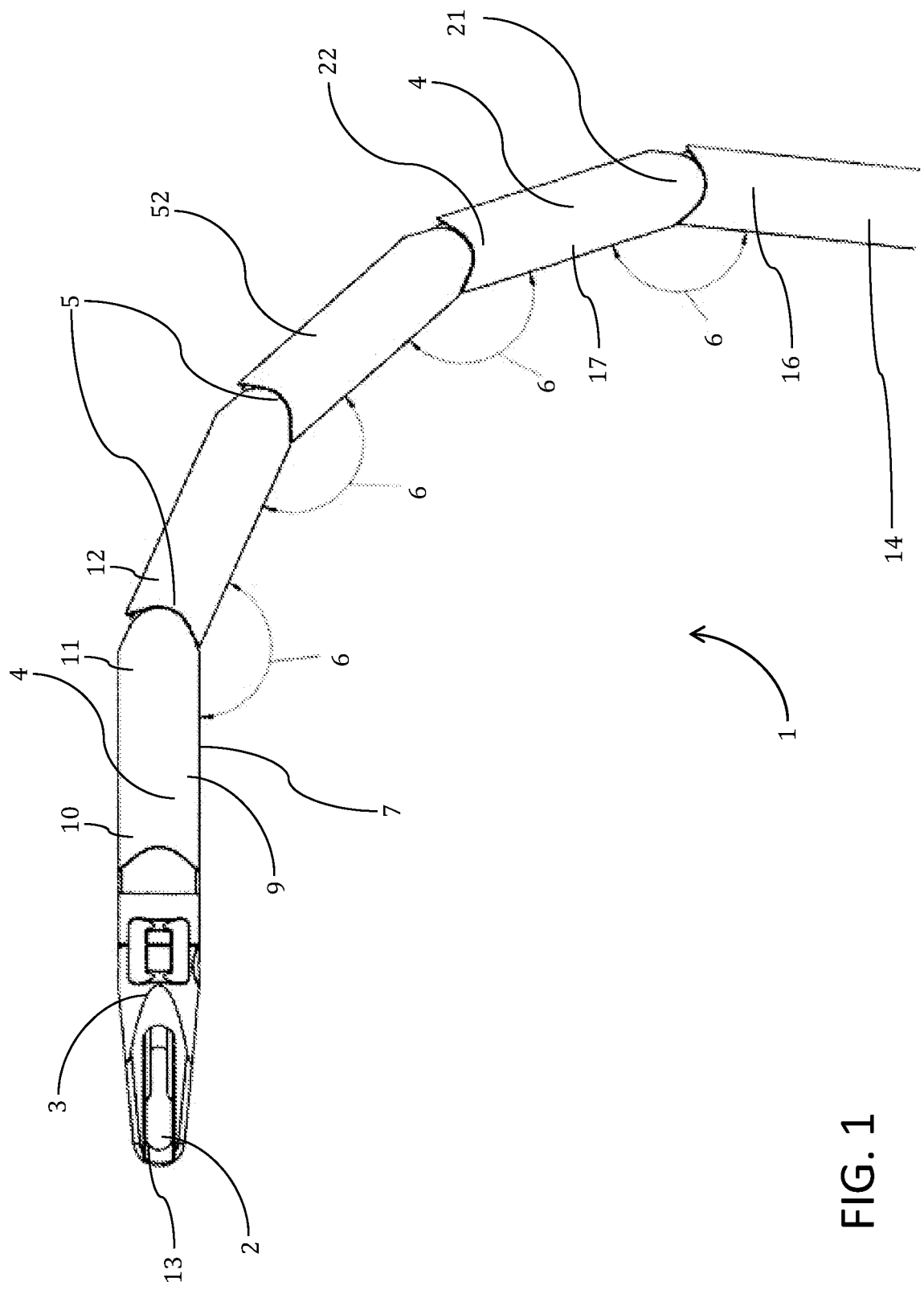
FIG. 1 illustrates a top view of the articulating steerable clip applier showing the separate angles of movement by different phalanges with covers.
Figure 2:
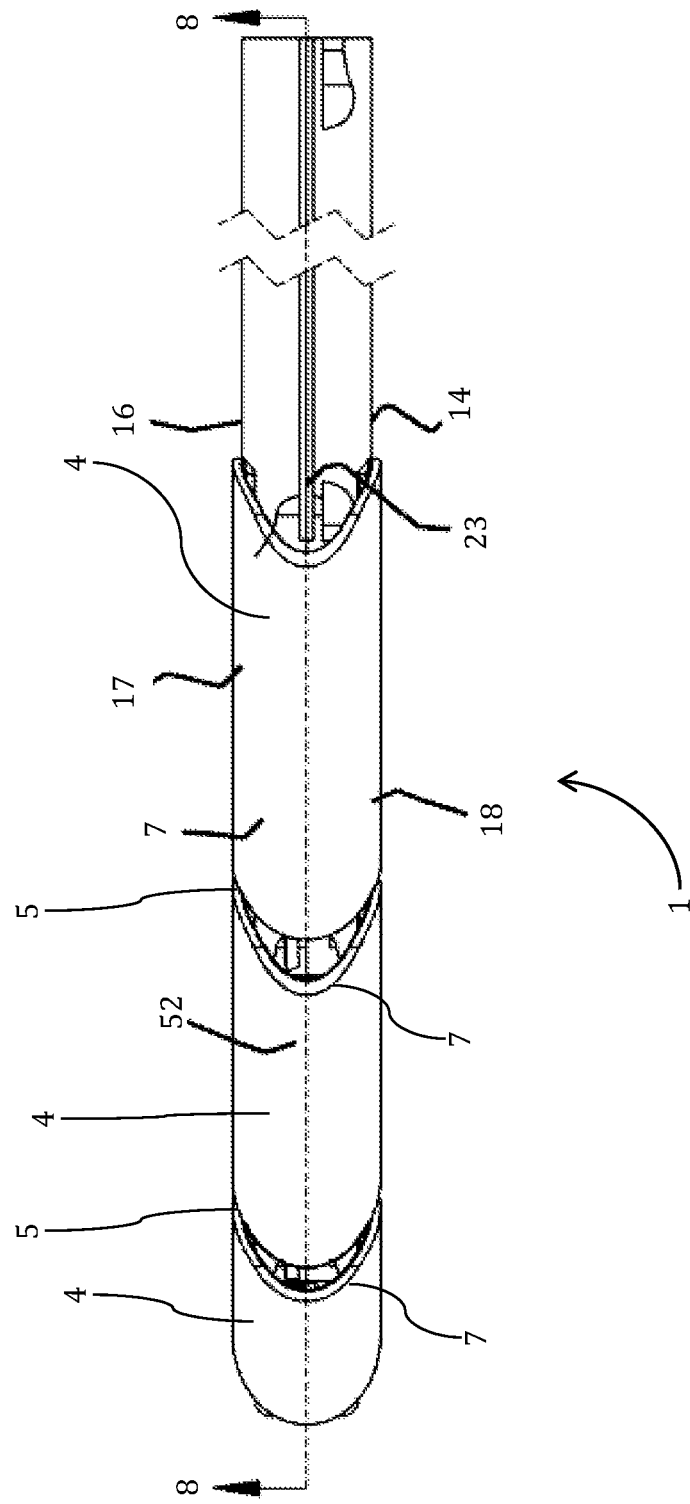
FIG. 2 illustrates a side view of the articulating steerable clip applier showing the separate angles of movement by different phalanges within a cover.
Figure 3:
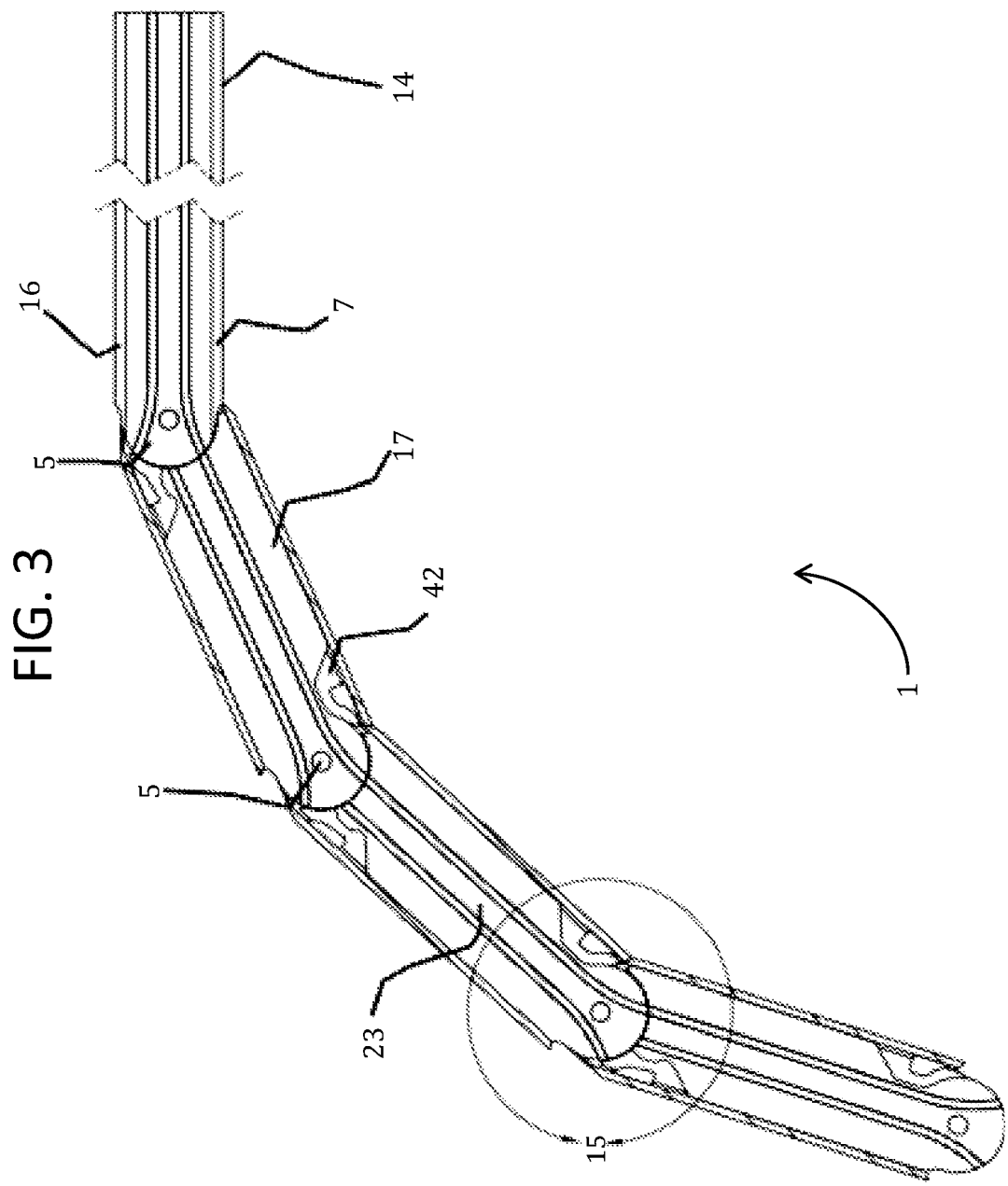
FIG. 3 illustrates a cross-sectional top view of the articulating steerable clip applier along the line 8 of FIG. 2.
Figure 4:
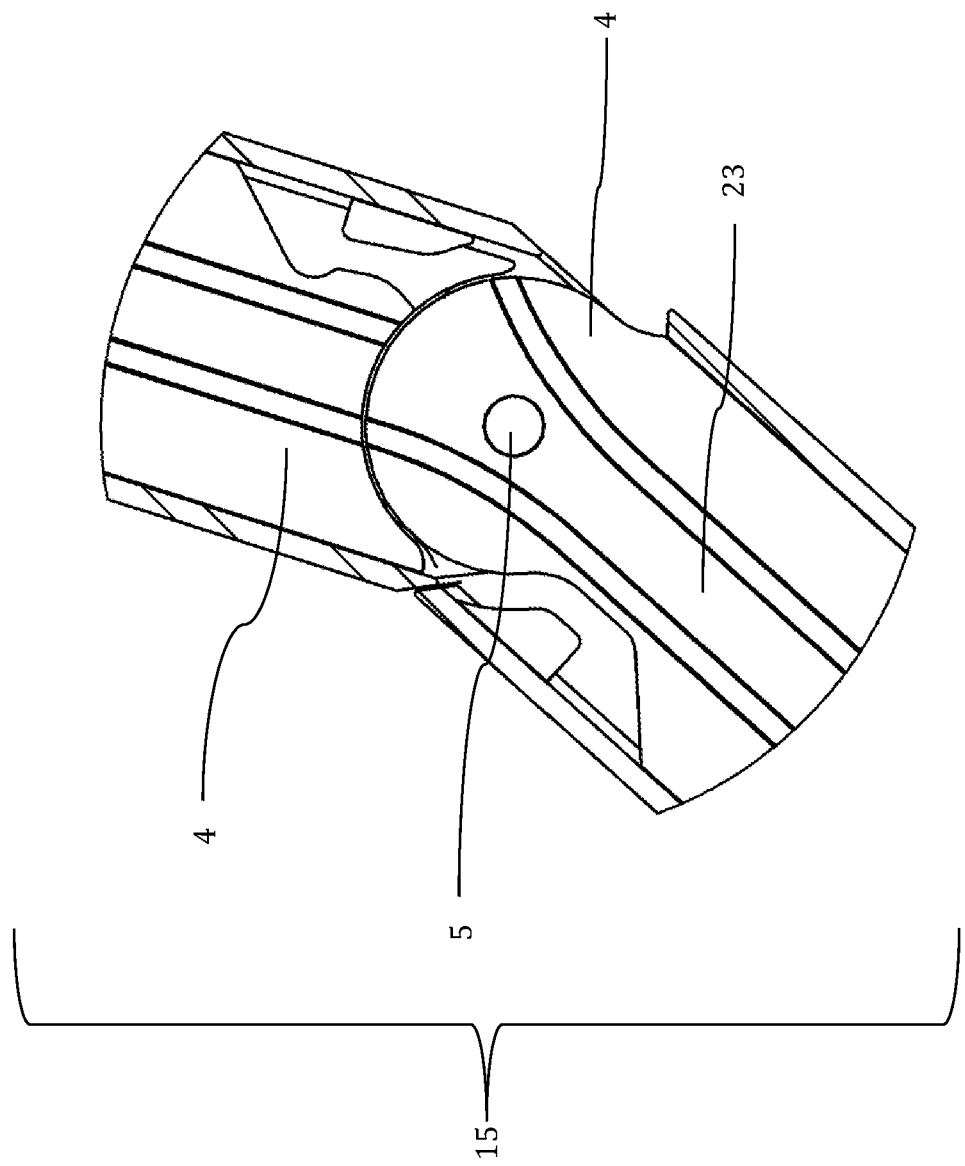
FIG. 4 illustrates an enlarged cross-sectional top view of line 15 of FIG. 3 showing the pivotable connection between two phalanges on the articulating steerable clip applier.
Figure 19:
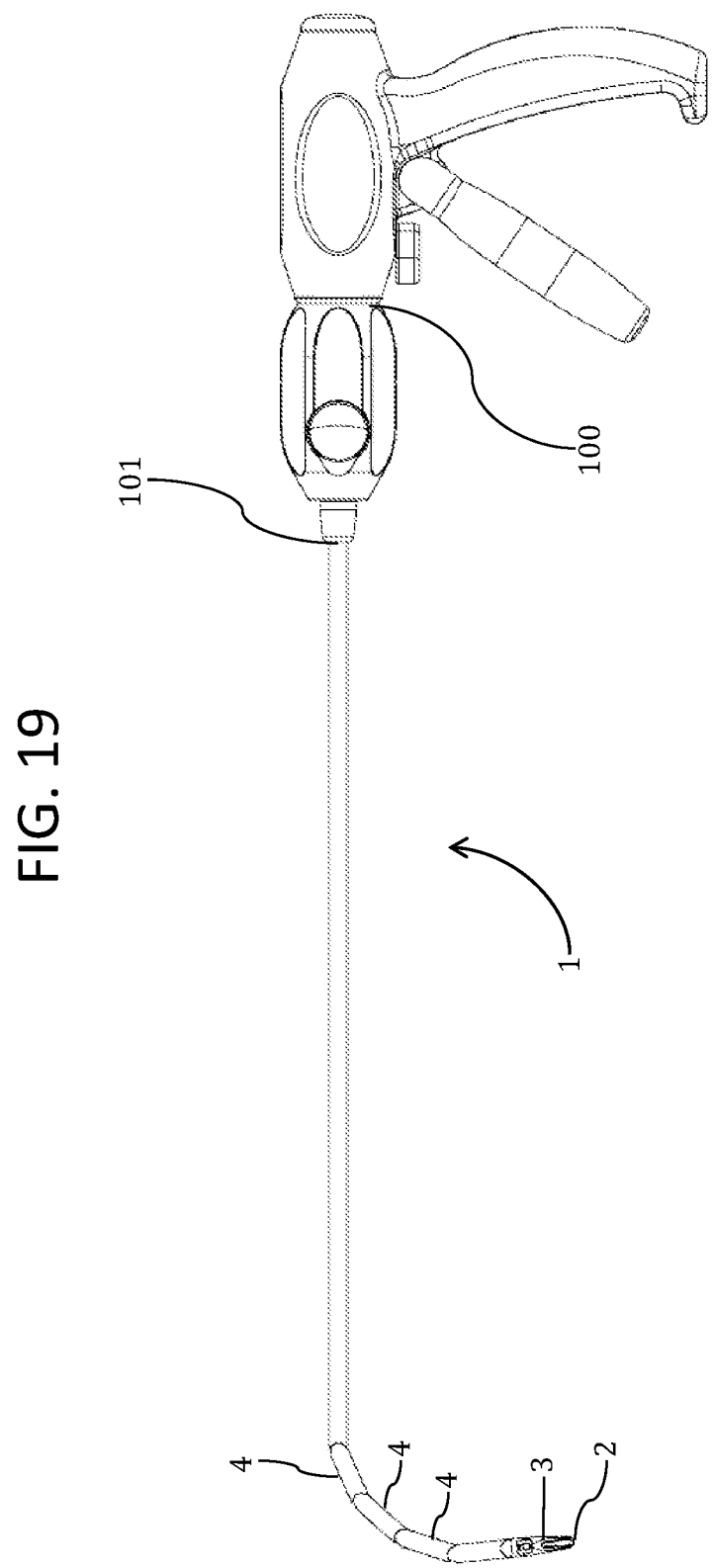
FIG. 19 illustrates a side view of an articulating steerable clip applier operatively attached on the proximal end to a user-operated handle.

FIGS. 1-3, 5, 6 and 11 illustrate a distal end 2 of the articulating steerable clip applier 1. The clip applier 1 is a long, narrow structure with a free distal end 2 adapted for coupling to an end effector, such as a surgical jaw assembly 3, and a proximal end 101 operatively coupled to a user-operated handle 100 (as shown in FIG. 19). The clip applier 1 is composed of a plurality of relatively short articulating members or phalanges 4 that are connected end to end by pivoting links 5 and capable of angulations 6 relative to one another when subjected to a tensile force. FIG. 3 illustrates a cross-sectional top view of the articulating steerable clip applier along the line 8 of FIG. 2. FIG. 4 illustrates an enlarged cross-sectional top view of pivoting point 5 showing the pivotable connection between two phalanges 4 on the articulating steerable clip applier 1 from line 15 of FIG. 3.

Figure 17:
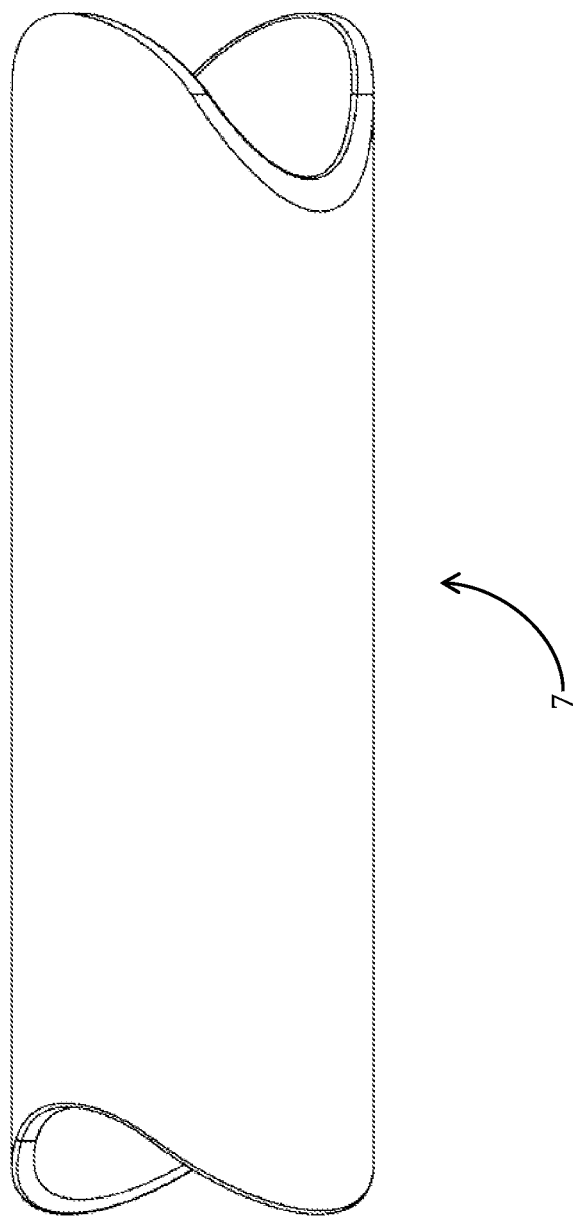
FIG. 17 illustrates a side view of a substantially circular elongate tubing that covers each individual phalange.
Figure 18:
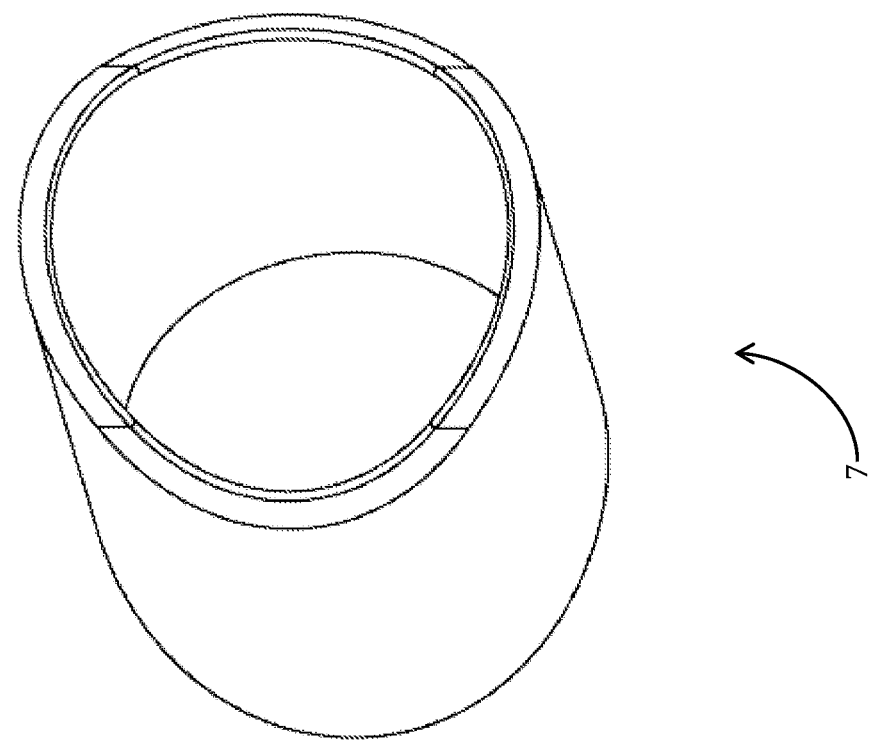
FIG. 18 illustrates a front view of a substantially circular elongate tubing that covers each individual phalange.

A sheath of elongate tubing 7 covers each individual phalange 4 such that the flexible joints of the phalange 4 are exposed. In one embodiment of the subject invention, this tubing 7 is composed of flexible materials. In another embodiment of the subject invention, this tubing 7 is composed of inflexible materials. Accordingly, the plurality of phalanges 4 is covered with a plurality of tubings 7. One embodiment of the tubing 7 is shown in FIGS. 17 and 18. A single flexible tubing (not shown) may cover the entire plurality of phalanges of the clip applier 1.

The distal end 2 of the articulating steerable clip applier 1 contains a final phalange 9. The final phalange 9 has a distal end 10 adapted for coupling to an end effector, such as a surgical jaw assembly 3, and a proximal end 11 that is attached to an adjacent proximal phalange 12. The distal tip 13 of the jaw assembly 3 is a surgical clip applicator for applying a surgical clip to a blood vessel (not shown).

The proximal end of the articulating steerable clip applier 1 contains an initial phalange 14. The initial phalange 14 has a proximal end 101 operatively coupled to a user-operated handle 100 and a distal end 16 that is attached to an adjacent first distal phalange 17.

Figure 11:
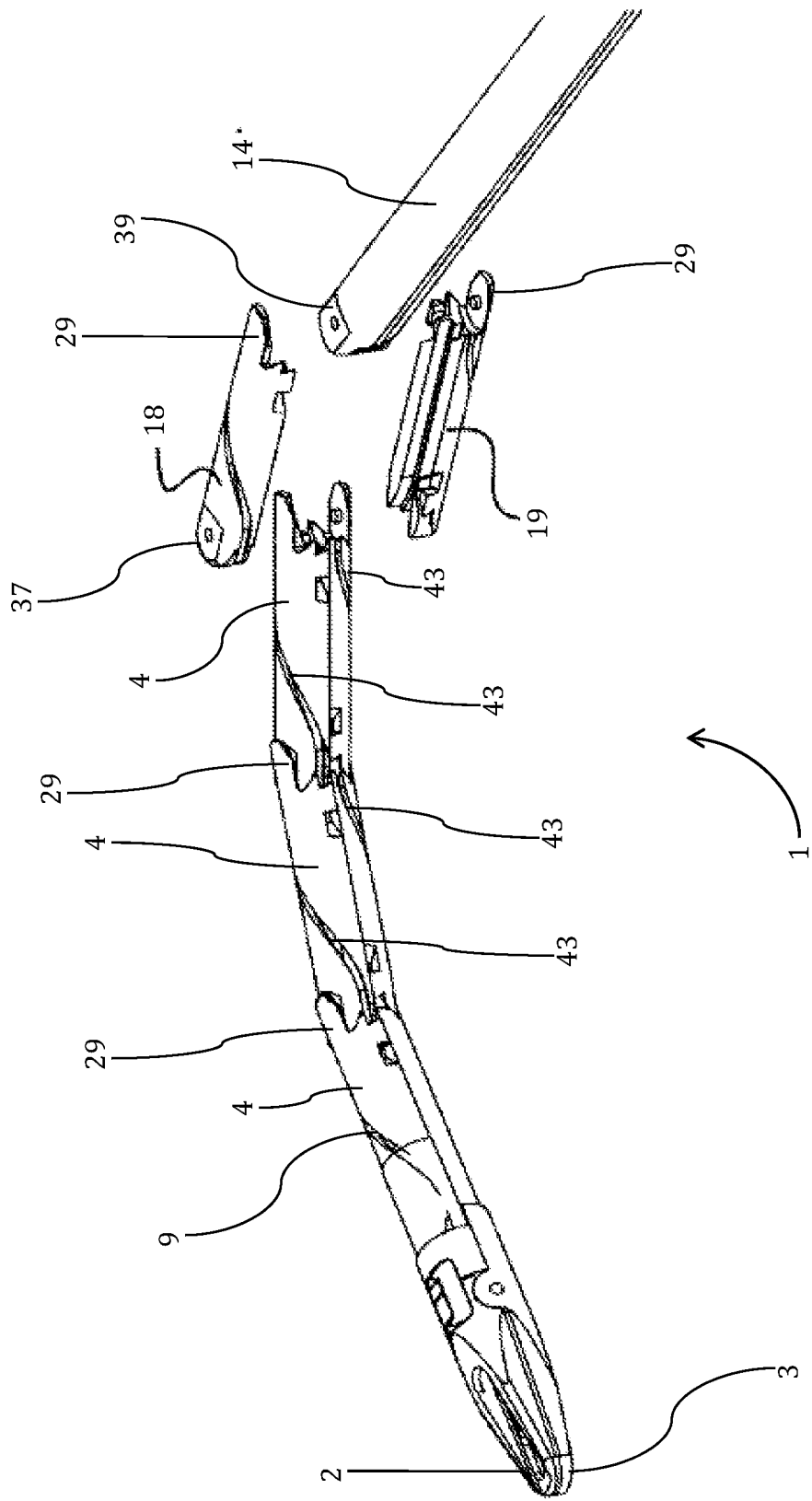
FIG. 11 illustrates a perspective view of the articulating steerable clip applier showing an individual phalange separated into the top and bottom half-phalanges.
Figure 12:
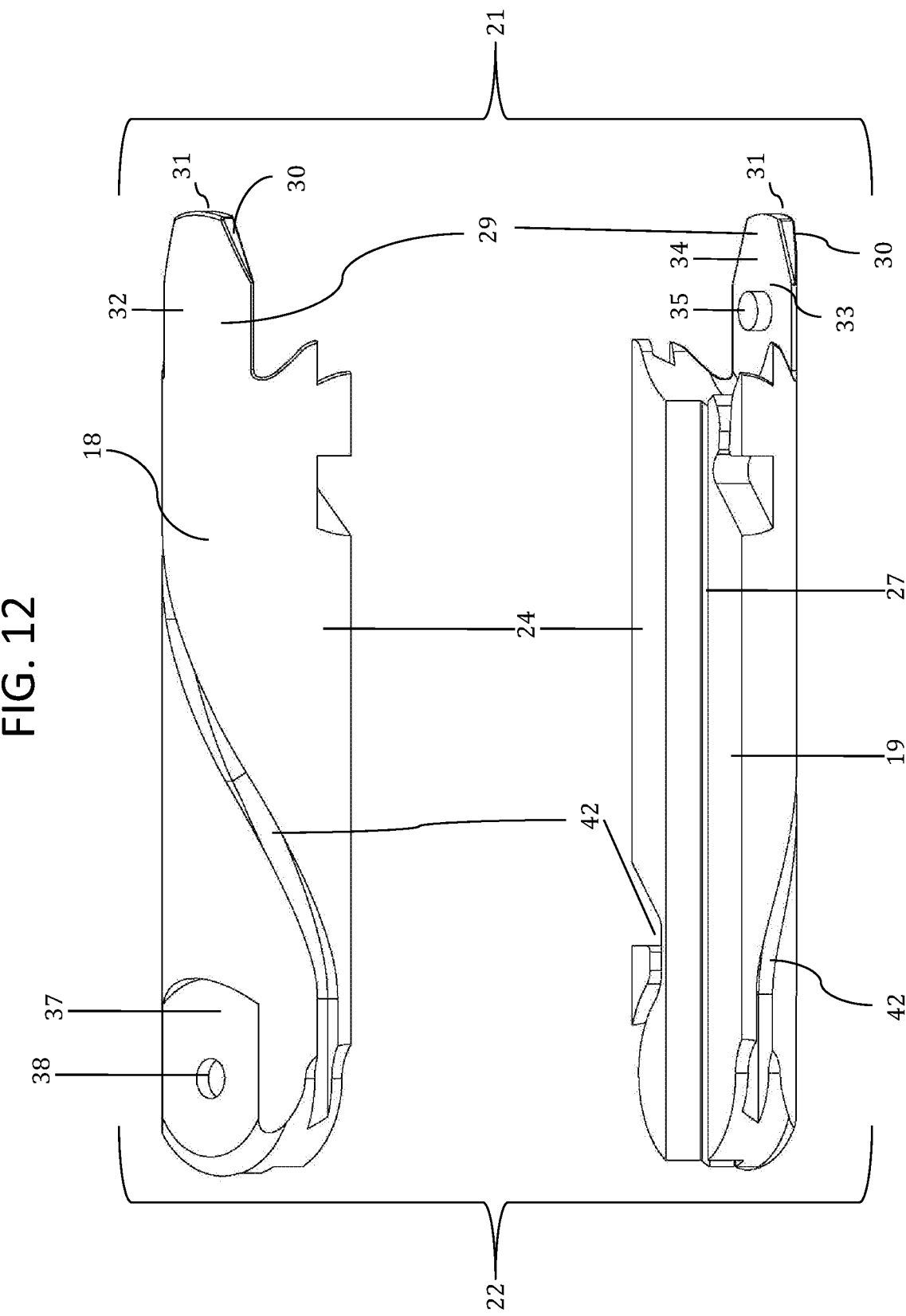
FIG. 12 illustrates a perspective view of a top half-phalange and a bottom half phalange of the articulating steerable clip applier.
Figure 13:
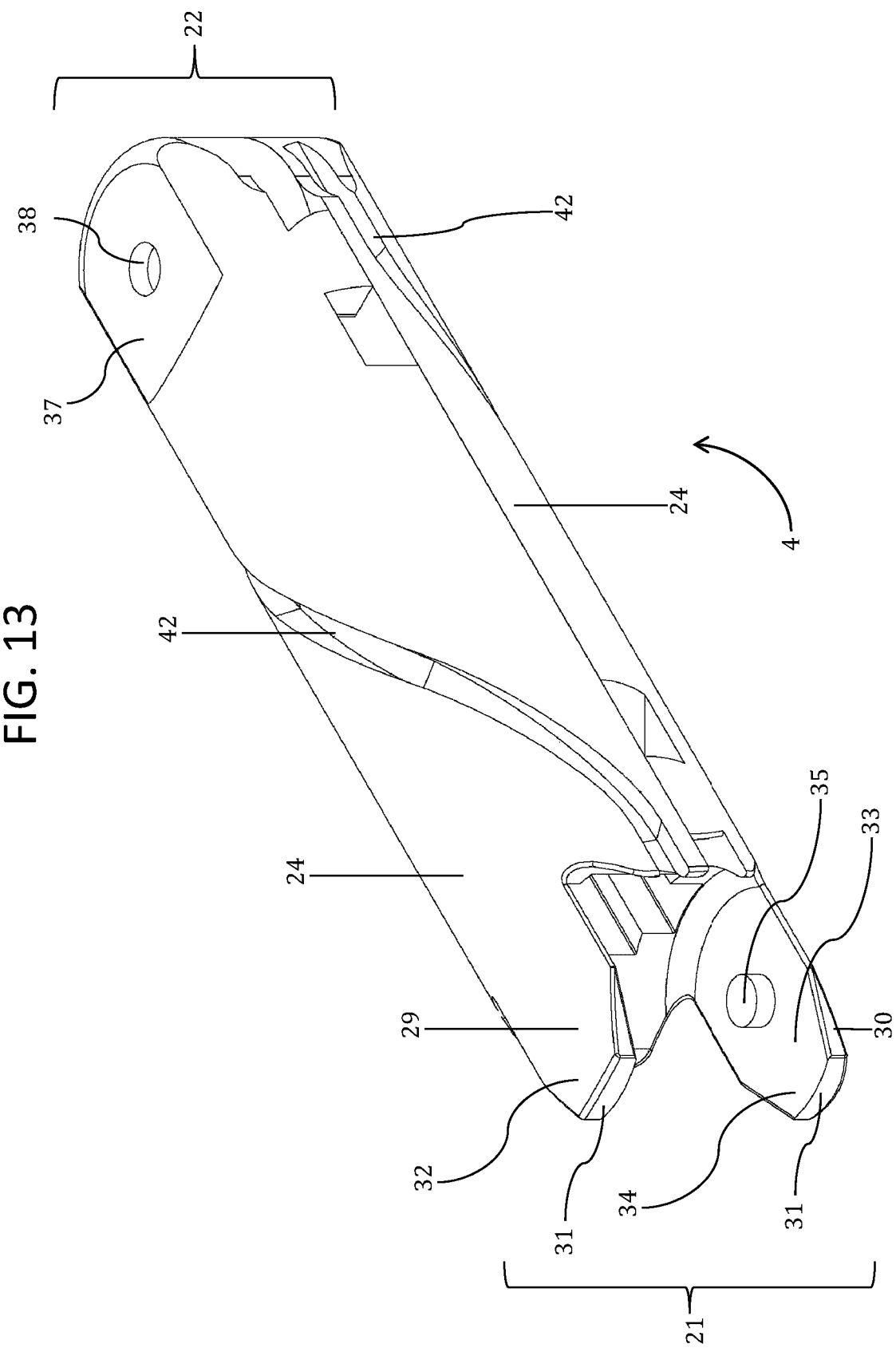
FIG. 13 illustrates a perspective view of a phalange comprising assembled top half and bottom half phalanges of the articulating steerable clip applier.

FIGS. 11-13 illustrate individual phalanges 4 spaced apart, but the phalanges 4 are disposed in the articulating clip applier 1 so that the distal end of each proximal phalange 4 co-acts with the proximal end of the adjacent distal phalange 4.

Each phalange 4 has a generally cylindrical configuration and is symmetrical about a longitudinal axis. Each phalange 4 has an exterior surface 18, described more fully below, and an interior surface 19 that defines a lumen 20 extending between the proximal end 21 and distal end 22. FIG. 10 illustrates a vertical cross-sectional view of an individual phalange 4 at line 18 of FIG. 9. The plurality of lumens 20 of each phalange 4 forms an internal longitudinal passage 23 in the articulating clip applier 1. Longitudinal passage 23 permits actuators, surgical clips, surgical clip carrying assemblies and other functional elements to pass through clip applier 1 and to control the operation of clip movement, clip ligation or phalange articulation. Each phalange 4 is composed of two half phalanges 24. As shown in FIG. 12, each half phalange 24 has the same structure: a curved exterior surface 18 and a generally planar interior surface 19. Each half phalange 24 has a substantially half-round or half-elliptical cross-sectional configuration so that an assembled phalange 4 has a substantially cylindrical configuration. The interior surface 19 of each half phalange 24 contains a longitudinal channel 27.

The proximal end 21 of the exterior surface 18 of each half phalange 24 contains an extension 29. The extension 29 may have angled sides 30 that form a curved end 31. The top surface 32 of each extension 29 has a curvature that is substantially the same as the curvature of the exterior surface 18. The bottom 33 of each extension 29 has a substantially flat planar surface 34. The bottom 34 of each extension 29 further has a substantially cylindrical protrusion 35.

The distal end 22 of each half phalange 24 contains a substantially flat planar surface 37 that is lowered from the curved exterior surface 18. The substantially flat planar surface 37 has a substantially circular internal bore 38 with a diameter that is generally larger than the diameter of the cylindrical protrusion 35.

A phalange 4 is assembled by attaching the interior surfaces 19 of two half phalanges 24 to one another so that the two longitudinal channels 27 on each interior surface 19 of each half phalange 24 form the lumen 20. An assembled phalange 4 will have two extensions 29 on the proximal end 21, with their respective substantially cylindrical protrusions 35 facing each other. The substantially flat planar surfaces 37 of the distal end 22 will be on opposing sides of the assembled phalange 4.

In one embodiment of the subject invention, the phalanges 4 are composed of injected-molded plastic.

As shown in FIGS. 3 and 11, the plurality of phalanges 4 is connected end to end by pivoting links 5 in the following manner:

The initial phalange 14 has a proximal end 101 attached to a user-operated handle 100 (shown in FIG. 19). The distal end 16 of the initial phalange 14 has substantially flat planar surfaces 39 on the top and bottom of the exterior surface 18. The substantially flat planar surfaces 39 each have a substantially circular internal bore 41 with a diameter that is generally larger than the diameter of the cylindrical protrusion 35.

The clip applier 1 is assembled by placing the two substantially cylindrical protrusions 35 on the proximal end 21 of the first distal phalange 17 into the internal bores 41 on opposing sides on the distal end 16 of the initial phalange 14. This pivoting link 5 attaches the first distal phalange 17 to the initial phalange 14.

The proximal end 21 of the first distal phalange 17 may pivot with respect to the initial phalange 14. The two substantially cylindrical protrusions 35 may rotate within the internal bores 41. The substantially flat planar surfaces 34 of each extension 29 rotate freely on the substantially flat planar surfaces 39 on opposing sides of the initial phalange 14.

Second, third and subsequent distal phalanges 4, as desired, are added to the first distal phalange 17 as follows: the two substantially cylindrical protrusions 35 on the proximal end 21 of a subsequent phalange 4 are placed into the internal bores 38 on opposing sides on the distal end 22 of the preceding proximal phalange 4.

As shown in FIGS. 1, 3, 5, 6 and 7, the proximal ends 21 of all subsequent distal phalanges 4 may pivot with respect to distal ends 22 of their respective adjacent proximal phalanges 4. The protrusions 35 on the proximal end 21 of each subsequent distal phalange 4 may rotate within the internal bores 38 on the distal end 22 of the adjacent proximal phalange 4. The substantially flat planar surfaces 34 of each extension 29 rotate freely on the substantially flat planar surfaces 37 of the adjacent proximal phalange 4.

Figure 9:
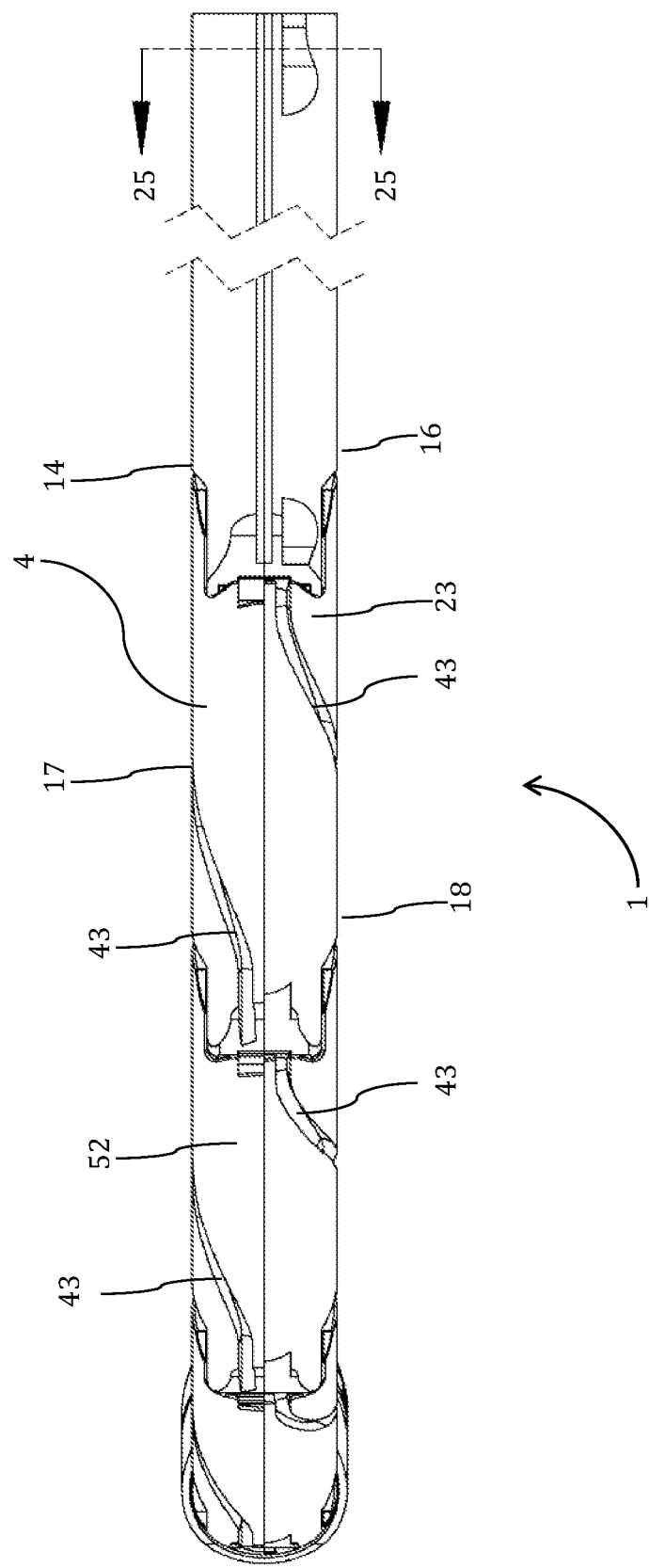
FIG. 9 illustrates a side view of the articulating steerable clip applier showing the opposing spiraled grooves which contain the tension wires.
Figure 10:
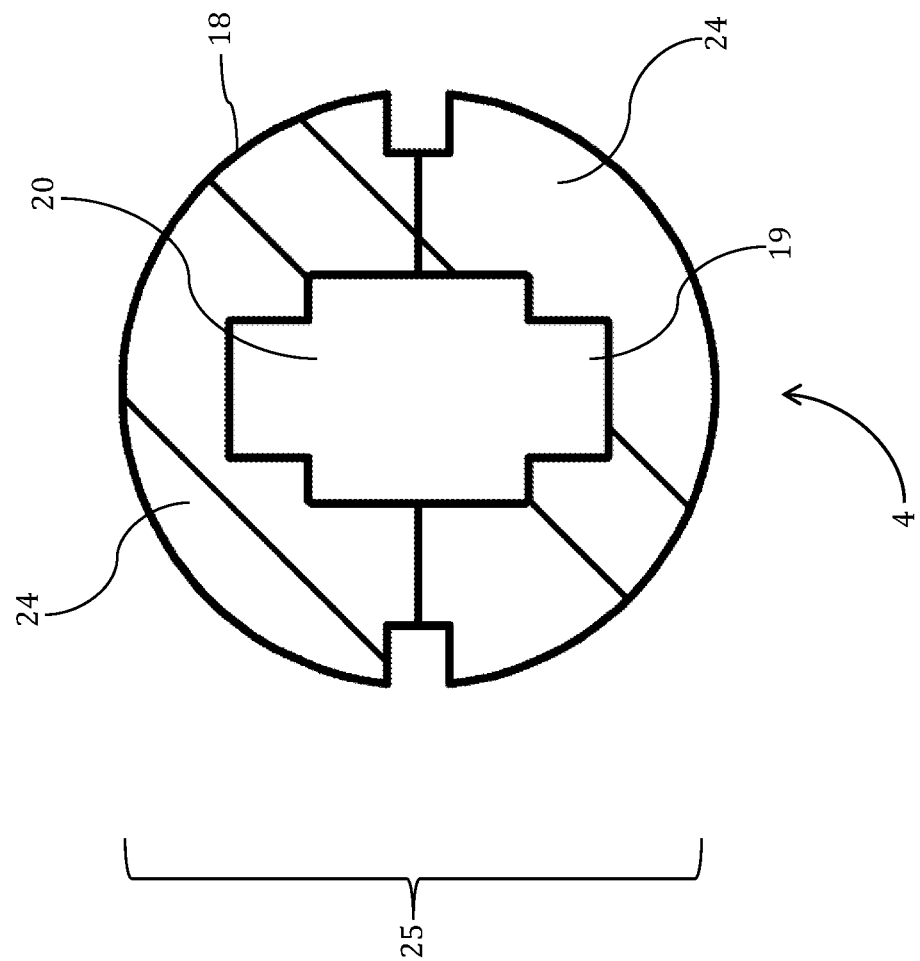
FIG. 10 illustrates a vertical cross-sectional view of an individual phalange at line 18 of FIG. 9 which contains a lumen that allows actuators, surgical clips, surgical clip carrying assemblies and other functional elements to pass through and operate to control clip movement, clip ligation or phalange articulation.

As shown in FIGS. 9, 12 and 13, the exterior surface 18 of each half phalange 24 contains at least one axially extending s-shaped groove 42 or channel. The curve of the s-shaped groove 42 traverses the width and length of the exterior surface 18 of the half phalange 24. The s-shaped groove 42 begins on one side of the exterior surface 18 at the proximal end 21 of the half phalange 24, axially extends and curves over the exterior surface 18 to the opposing side of the exterior surface on the distal end 22 of the half phalange 24.

Once a phalange 4 is assembled, it has two grooves 42 on both exterior surfaces 18 that axially extend in the phalange 4 in opposing s-shaped curves. Once the plurality of phalanges 4 is assembled, the two s-shaped grooves 42 form two continuous axially extending spiral shaped channels 43 that curve in opposing directions from each other.

A tension cable or wire is inserted into each spiral shaped channel 43, to provide steering control for the plurality of phalanges 4. Tension wire is preferably made from a super-elastic material, e.g., nickel titanium alloy, braided stainless steel, a single stainless steel wire, Kevlar, a high tensile strength monofilament thread, or combinations thereof.

Figure 5:
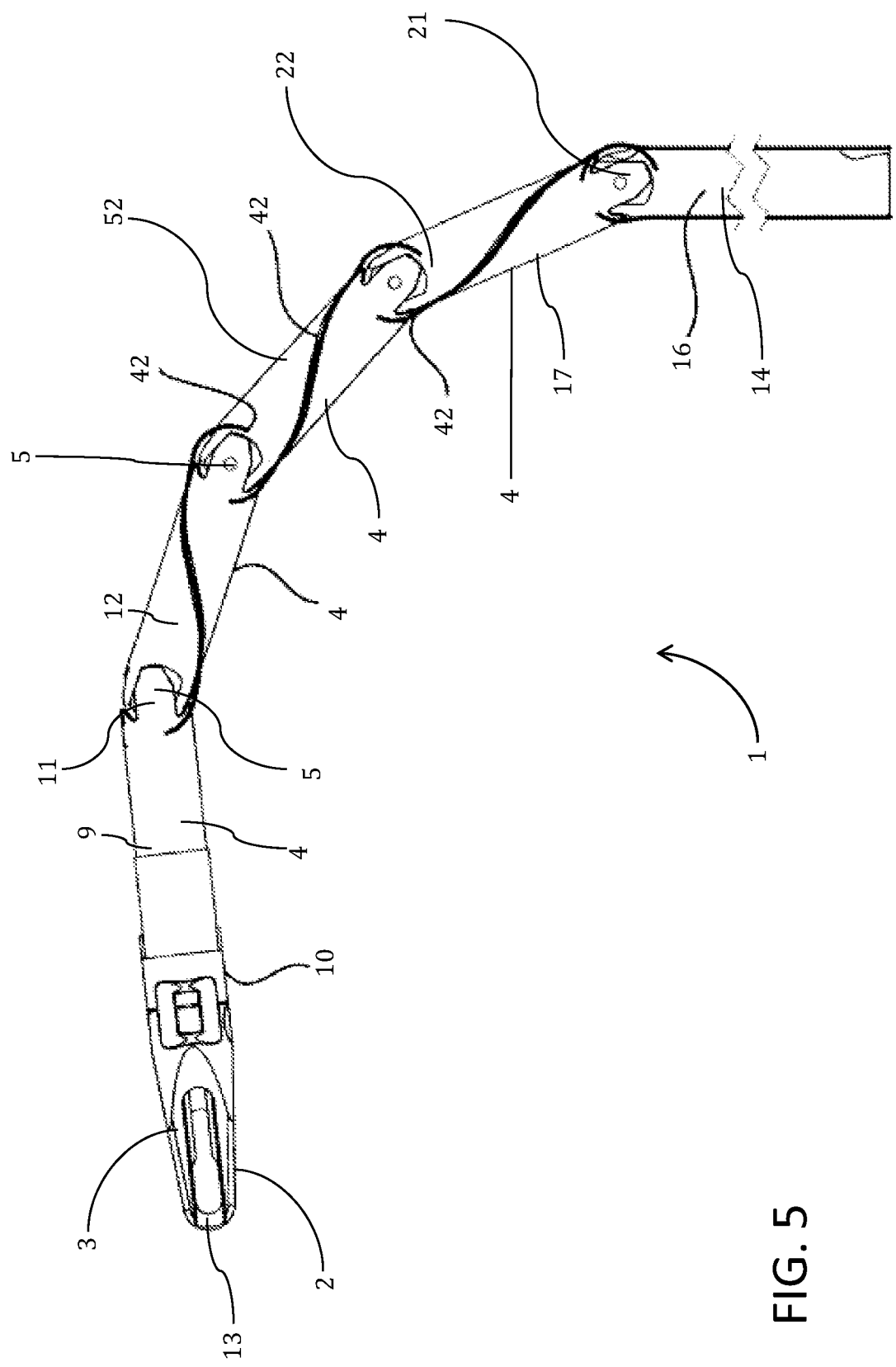
FIG. 5 illustrates another top view of the articulating steerable clip applier showing the separate angles of movement by individual phalanges guided by tension wires connected from a first phalange traversing through opposing spiraled grooves on the next distal phalange to attach to a second distal phalange.
Figure 6:
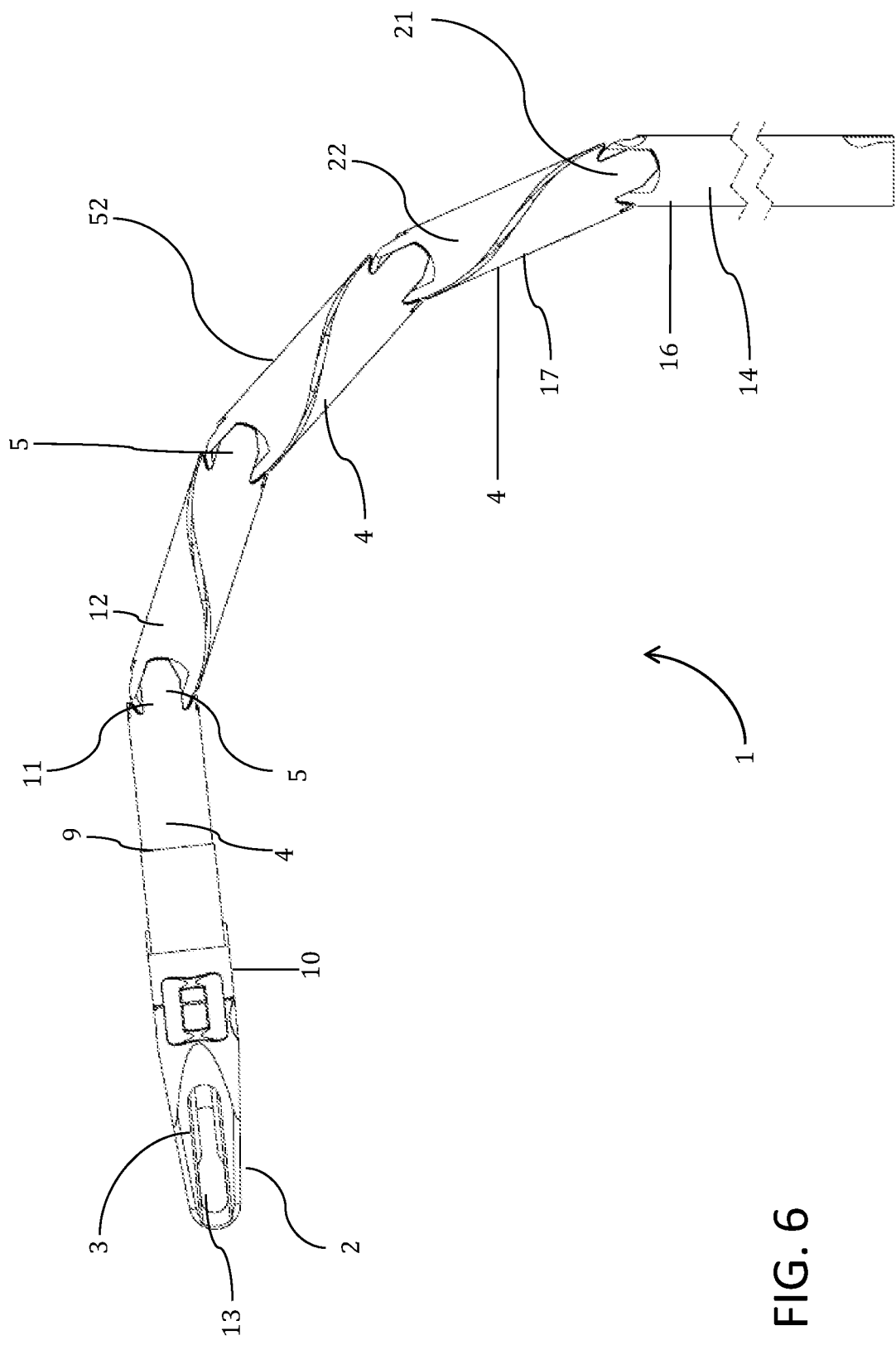
FIG. 6 illustrates another top view of the articulating steerable clip applier showing the separate angles of movement by individual phalanges with opposing spiraled grooves for holding the tension wires.
Figure 7:
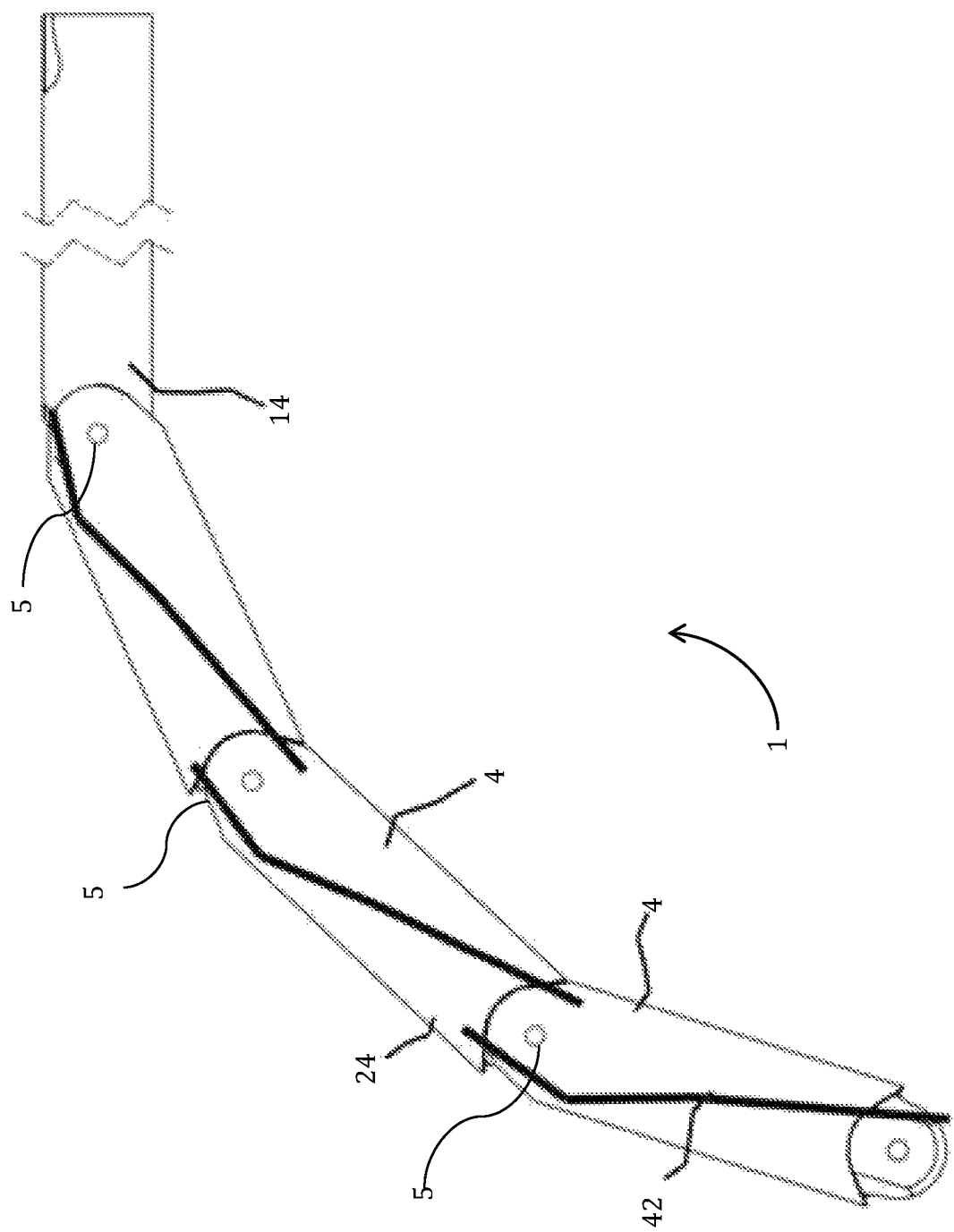
FIG. 7 illustrates a top view of connected adjacent phalanges of the articulating steerable clip applier without covers showing the separate angles of movement by different adjacent phalanges by flexible tension wires.
Figure 8:
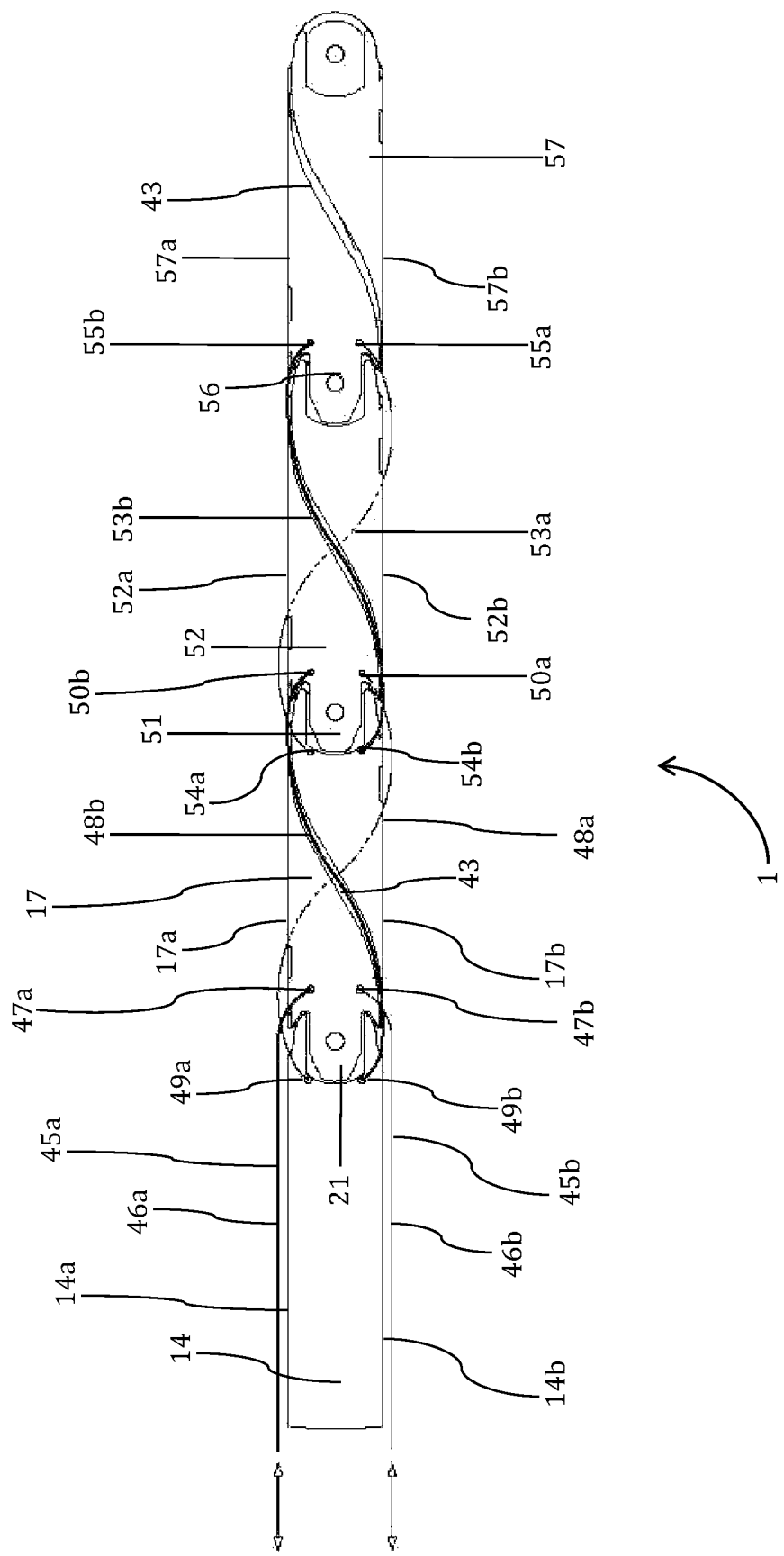
FIG. 8 illustrates the attachments of separate flexible tension wires on the separate phalanges of the articulating steerable clip applier, wherein each tension wire connects on its proximal end to one side of a first phalange, traverses through opposing spiraled grooves on the next distal phalange and attaches on its distal end to the opposing side of a second distal phalange.

As shown in FIGS. 5, 7 and 8 a first set of two wires 45a and 45b are connected on their respective proximal ends 46a and 46b to the initial phalange 14 and connected on their respective distal ends 47a and 47b to the proximal end 21 of the adjacent first distal phalange 17. The proximal end 46a of wire 45a is attached to one side 14a of the initial phalange 14 and the distal end 47a of wire 45a is attached to the side 17a of the first distal phalange 17 on its proximal end 21. The proximal end 46b of wire 45b is attached to the opposing side 14b of the initial phalange 14 and the distal end 47b of wire 45b is attached to the side 17b of the first distal phalange 17 on its proximal end 21. When wire 45a is pulled, this tensile force causes the first distal phalange 17 to pivot back and forth at its proximal end 21 towards side 17a, away from side 14b. When wire 45b is pulled, this tensile force causes the first distal phalange 17 to pivot back and forth at its proximal end 21 towards side 17b, away from side 14a. Furthermore, each subsequently attached phalange 4 is moved by the same pivoted angle above, when either wire 45a or 45b is pulled.

A second set of two wires 48a and 48b are connected on their respective proximal ends 49a and 49b to the initial phalange 14 and connected on their respective distal ends 50a and 50b to the proximal end 51 of the second distal phalange 52, which is adjacent to phalange 17. The wires 48a and 48b are inserted into the two spiral shaped channels 43 that curve in opposing directions. The proximal end 49a of wire 48a is attached to one side 14a of the initial phalange 14 and the distal end 50a of wire 48a is attached to the opposing side 52b of the second distal phalange 52 on its proximal end 51. The proximal end 49b of wire 48b is attached to the opposing side 14b of the initial phalange 14 and the distal end 50b of wire 48b is attached to the opposing side 52a of the second distal phalange 52 on its proximal end 51. When wire 48a is pulled, this tensile force causes the second distal phalange 52 to pivot back and forth at its proximal end 51 towards side 52b, away from side 14a. When wire 48b is pulled, this tensile force causes the second distal phalange 52 to pivot back and forth at its proximal end 51 towards side 52a, away from side 14b. Furthermore, each subsequently attached phalange 4 is moved by the same pivoted angle above, when either wire 48a or 48b is pulled. Since the proximal end and the distal end of each wire 48a or 48b is attached to opposing sides of the initial phalange 14 and the second distal phalange 52, pulling either wire 48a or 48*b* causes the second distal phalange 52 to pivot in the direction of the distal end of the wire and away from the proximal end of the wire.

A third set of two wires 53*a* and 53*b* are connected on their respective proximal ends 54*a* and 54*b* to the first distal phalange 17 and connected on their respective distal ends 55*a* and 55*b* to the proximal end 56 of the third distal phalange 57, which is adjacent to second distal phalange 52. The wires 53*a* and 53*b* are inserted into the two spiral shaped channels 43 that curve in opposing directions. The proximal end 54*a* of wire 53*a* is attached to one side 17*a* of the first distal phalange 17 and the distal end 55*a* of wire 53*a* is attached to the opposing side 57*b* of the third distal phalange 57 on its proximal end 56. The proximal end 54*b* of wire 53*b* is attached to the opposing side 17*b* of the first distal phalange 17 and the distal end 55*b* of wire 53*b* is attached to the opposing side 57*a* of the third distal phalange 57 on its proximal end 56. When wire 53*a* is pulled, this tensile force causes the third distal phalange 57 to pivot back and forth at its proximal end 56 towards side 57*b*, away from side 17*a*. When wire 53*b* is pulled, this tensile force causes the third distal phalange 57 to pivot back and forth at its proximal end 56 towards side 57*a*, away from side 17*b*. Furthermore, each subsequently attached phalange 4 is moved by the same pivoted angle above, when either wire 53*a* or 53*b* is pulled. Since the proximal end and the distal end of each wire 53*a* or 53*b* is attached to opposing sides of the first distal phalange 17 and the third distal phalange 57, pulling either wire 53*a* or 53*b* causes the third distal phalange 57 to pivot in the direction of the distal end of the wire and away from the proximal end of the wire.

Additional sets of two wires may be connected on their proximal ends to a proximal phalange and connected on their distal end to the proximal end of phalange that is two phalanges distal from the proximal phalange. The wires are inserted into the two spiral shaped channels 43 that curve in opposing directions. The proximal end of each wire is attached to one side of the proximal phalange. The distal end of each wire is attached to the opposing side of the phalange that is two phalanges distal from the proximal phalange. When each wire is pulled, this tensile force causes the phalange that is two phalanges distal from the proximal phalange to pivot back and forth at its proximal end. The direction of this pivoting is towards the distal end attachment of each wire and away from the proximal end attachment of each wire.

A user may actuate the wires above to pivot all the remaining phalanges 4 such that the angle 6 between the distal end of a preceding phalange and the proximal end of the subsequent phalange in the clip applier is substantially equivalent. FIGS. 1 and 2 illustrate the separate, but identical, angles of movement 6 by individual phalanges 4.

As each individual phalange 4 pivots by an equivalent angle 6, the sum of these angles 6 causes the distal end 2 of the clip applier 1 to pivot by a large angle or a cascading actuation effect, as shown in FIG. 1.

Figure 14:
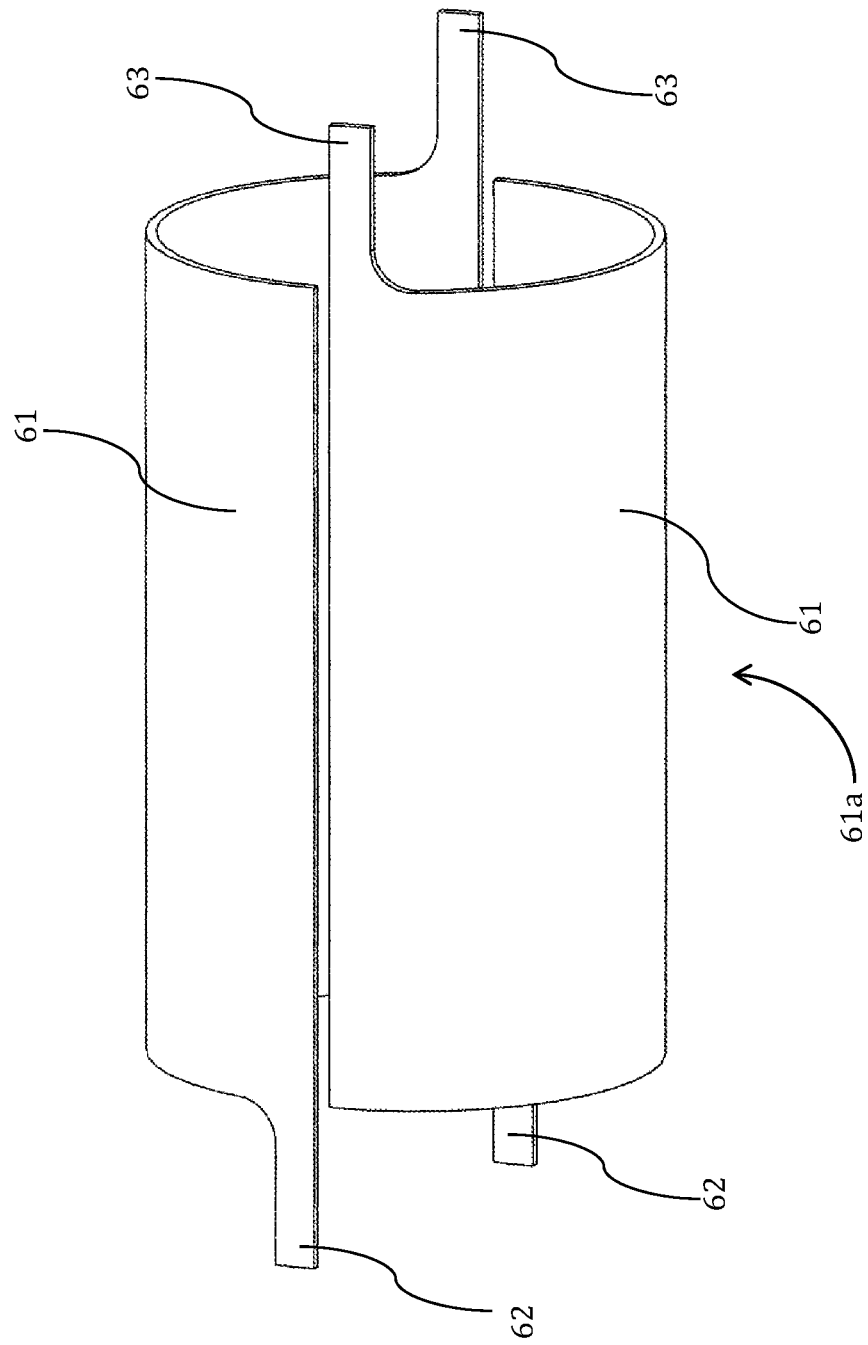
FIG. 14 illustrates a side view of a top and bottom semi-circular connecting ligaments of an individual phalange.
Figure 15:
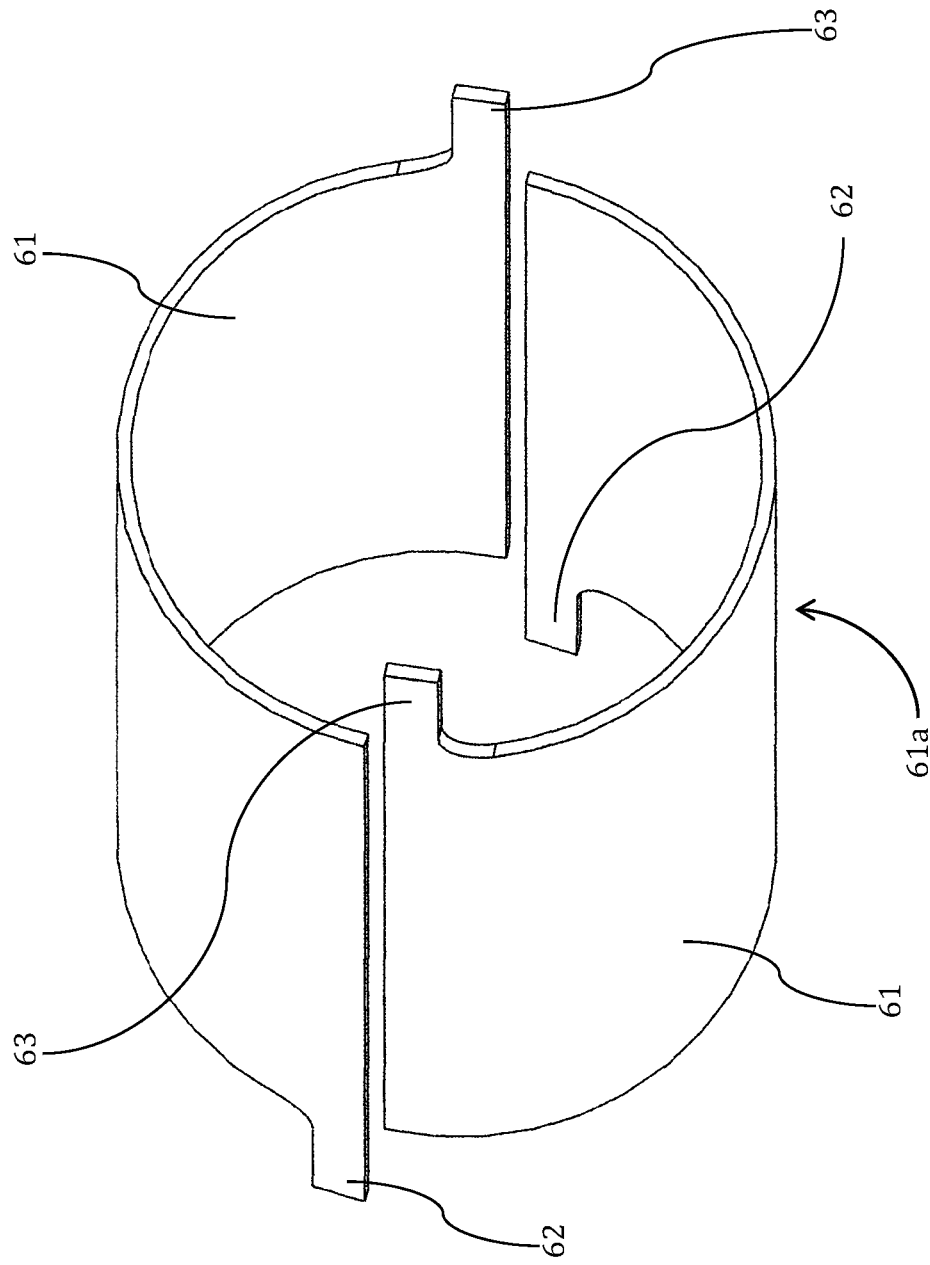
FIG. 15 illustrates a front view of a top and bottom semi-circular connecting ligaments of an individual phalange.
Figure 16:
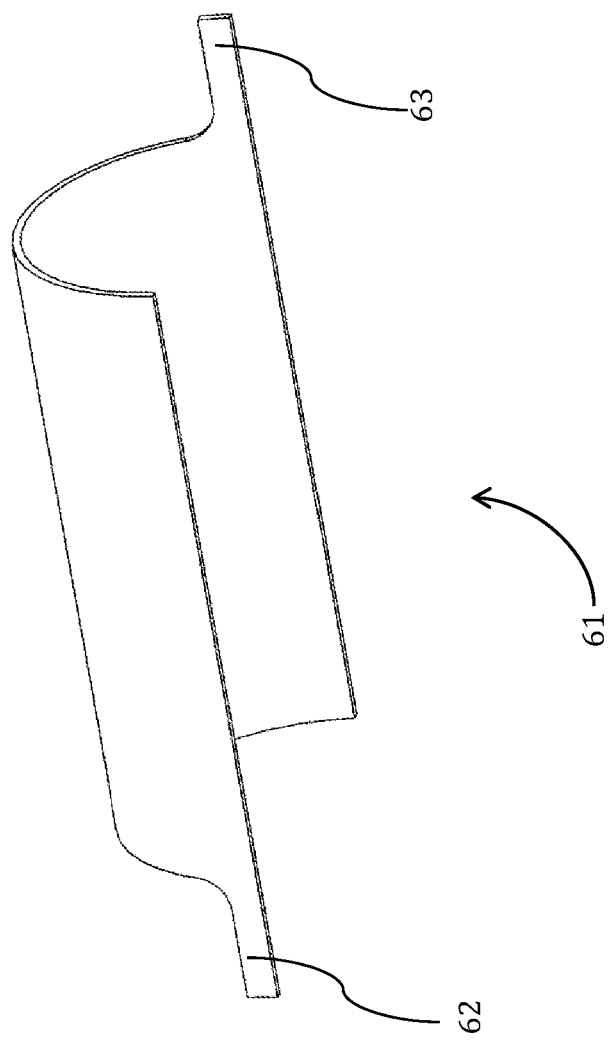
FIG. 16 illustrates a side view of a top semi-circular connecting ligament of an individual phalange.

In another embodiment of the subject invention, as shown in FIGS. 14-16, the tension wires above may be replaced by semi-circular connecting ligaments 61. Each individual phalange 4 may be substantially covered with two semi-circular connecting ligaments 61. FIGS. 14 and 15 illustrate two semi-circular connecting ligaments 61 in an opposing top-bottom configuration 61*a* to cover an individual phalange (not shown).

Each semi-circular connecting ligament 61 has a flexible tip 62 on its proximal end and a flexible tip 63 on its distal end. Furthermore, flexible tips 62 and 63 are on opposing sides of each semi-circular connecting ligament 61.

In the opposing top-bottom configuration 61*a*, flexible tips 62 are attached to the distal end of a proximal phalange on opposing sides, an adjacent distal phalange is substantially covered by the two opposing semi-circular connecting ligaments 61, and flexible tips 63 are attached to the proximal end of a second distal phalange on opposing sides.

Each flexible tip 62 is attached to one side of the proximal phalange and each flexible tip 63 is attached to the opposing side of the second distal phalange. When a flexible tip 62 is pulled, this force causes the second distal phalange to pivot at its proximal end. The direction of this pivoting is away from the flexible tip 62 that is pulled.

A user may actuate the flexible tips 62 above to pivot all the remaining phalanges 4 such that the angle 6 between the distal end of a preceding phalange and the proximal end of the subsequent phalange in the clip applier is substantially equivalent. FIGS. 1 and 2 illustrate the separate, but identical, angles of movement 6 by individual phalanges 4.

In one embodiment of the subject invention, the narrow plurality of phalanges 4 may easily fit within respective envelopes of 10 mm and 3 mm MIS instrumentation, while retaining flexible movements within a patient.

What is claimed is:

1. A device comprising:
    a handle extending along a central longitudinal axis;
    a first phalanx movably coupled to the handle;
    a second phalanx movably coupled to the first phalanx;
    wherein each phalanx comprises two s-shaped grooves on opposite sides of an exterior surface of the respective phalanx, wherein each s-shaped groove begins on a first side of a proximal end of the exterior surface and curves over the exterior surface to an opposing side of a distal end of the exterior surface;
    a first pair of semicircular connecting ligaments, each of which includes a proximal end and a distal end, the first pair of semicircular connecting ligaments being positioned in an opposite top-bottom configuration and in a covering relation over the first phalanx; and
    a second pair of semicircular connecting ligaments, each of which includes a proximal end and a distal end, the second pair of semicircular connecting ligaments being positioned in an opposite top-bottom configuration and in a covering relation over the second phalanx.

2. The device of claim 1, wherein the second phalanx moves at a same angle and in a same direction as the first phalanx, wherein the angle of the first phalanx is measured from the handle to the first phalanx, and the angle of the second phalanx is measured from the first phalanx to the second phalanx.

3. The device of claim 1, wherein each of the first phalanx and the second phalanx comprises a lumen, and the lumens form an internal longitudinal passage when connected.

4. The device of claim 1, wherein at least one of the first pair of semicircular connecting ligaments or second pair of semicircular connecting ligaments comprises a first flexible tip extending from the proximal end or from the distal end thereof.

5. The device of claim 4, further comprising a second flexible tip, wherein the first flexible tip extends from the proximal end of the at least one of the first pair of semicircular connecting ligaments or second pair of semicircular connecting ligaments, and the second flexible tip extends from the distal end of the at least one of the first pair of semicircular connecting ligaments or second pair of semicircular connecting ligaments.

6. The device of claim 5, wherein the first flexible tip extends from the proximal end of the at least one of the first pair of semicircular connecting ligaments or second pair of semicircular connecting ligaments on one side of the central longitudinal axis, and the second flexible tip extends from the distal end of the at least one of the first pair of semicircular connecting ligaments or second pair of semicircular connecting ligaments on the other side of the central longitudinal axis.

7. The device of claim 6, wherein a second one of the first pair of semicircular connecting ligaments or the second pair of semicircular connecting ligaments comprises a first flexible tip extending from the proximal end or from the distal end thereof.

8. The device of claim 7, further comprising a second flexible tip, wherein the first flexible tip extends from the proximal end of the second one of the first pair of semicircular connecting ligaments or the second pair of semicircular connecting ligaments, and the second flexible tip extends from the distal end of the second one of the first pair of semicircular connecting ligaments or the second pair of semicircular connecting ligaments.

9. The device of claim 8, wherein the first flexible tip extends from the proximal end of the second one of the first pair of semicircular connecting ligaments or the second pair of semicircular connecting ligaments on one side of the central longitudinal axis, and the second flexible tip extends from the distal end of the second one of the first pair of semicircular connecting ligaments or the second pair of semicircular connecting ligaments on the other side of the central longitudinal axis.

10. The device of claim 1, wherein each of the first pair of semicircular connecting ligaments or the second pair of semicircular connecting ligaments includes a first flexible tip extending from the proximal end thereof and a second flexible tip extending from the distal end thereof.

11. The device of claim 10, wherein each first flexible tip extends on opposite sides of the central longitudinal axis.

12. The device of claim 10, wherein each second flexible tip extends on opposite sides of the central longitudinal axis.

\* \* \* \* \*